United States Patent
Kosmatopoulos et al.

(10) Patent No.: US 12,048,737 B2
(45) Date of Patent: *Jul. 30, 2024

(54) **USE OF A VACCINE TARGETING A CRYPTIC TERT EPITOPE, FOR TREATING CANCER IN A HLA-A*0201-POSITIVE PATIENT HAVING A NON-IMMUNOGENIC TUMOR EXPRESSING TERT**

(71) Applicant: KRIPTIC PHARMACEUTICALS LIMITED, Dublin (IE)

(72) Inventors: Kostantinos (Kostas) Kosmatopoulos, Paris (FR); Jeanne Menez-Jamet, Montrouge (FR); Catherine Gallou, Bures-sur-Yvette (ER); Aude Rougeot, Bourg-la-Reine (FR)

(73) Assignee: KRIPTIC PHARMACEUTICALS LIMITED, Dublin (IE)

( * ) Notice: Subject to any disclaimer, the term of this patent is extended or adjusted under 35 U.S.C. 154(b) by 554 days.

This patent is subject to a terminal disclaimer.

(21) Appl. No.: 16/611,153

(22) PCT Filed: May 4, 2018

(86) PCT No.: PCT/EP2018/061602
§ 371 (c)(1),
(2) Date: Nov. 5, 2019

(87) PCT Pub. No.: WO2018/206461
PCT Pub. Date: Nov. 15, 2018

(65) Prior Publication Data
US 2020/0078454 A1   Mar. 12, 2020

(30) Foreign Application Priority Data

May 9, 2017 (EP) .................................... 17305526

(51) Int. Cl.
*A61K 39/00* (2006.01)
*C12N 5/0783* (2010.01)

(52) U.S. Cl.
CPC .... *A61K 39/001157* (2018.08); *C12N 5/0638* (2013.01); *A61K 2039/545* (2013.01); *A61K 2039/55* (2013.01); *A61K 2039/55566* (2013.01)

(58) Field of Classification Search
CPC ...... A61K 39/001157; A61K 2039/545; A61K 2039/55; C12N 5/0638
USPC ................. 424/185.1; 514/1.1, 19.3; 435/7.1
See application file for complete search history.

(56) References Cited

U.S. PATENT DOCUMENTS 8,663,645 B2 * 3/2014 Kosmatopoulos ........................... A61K 39/001122
424/277.1

OTHER PUBLICATIONS

Kotsakis et al. (2014) Lung Cancer, vol. 86, 59-66.*
Georgoulias et al. (2013) Clinical Lung Cancer, vol. 14 (4), 461-465.*
Gridelli et al. (2020) Brit. J. Canc., https://doi.org/10.1038/s41416-020-0785-y, pp. 1-6.*
Clinical Trial NCT01935154 (Version 7, submitted Dec. 8, 2015), Clinical Trials.gov, archive, pp. 1-11.*
Slota et al. (2011) Exp. Rev. Vaccines, vol. 10(3), 299-306. doi:10.1586/erv.10.169, pp. 1-14.*
Bolonaki et al., "Vaccination of patients with advanced non-small-cell lung cancer with an optimized cryptic human telomerase reverse transcriptase peptide," Journal of Clinical Oncology, 25: 2727-2734 (2007).
Cornet et al., "CpG oligodeoxynucleotides activate dendritic cells in vivo and induce a functional and protective baccine immunity against a TERT derived modified cryptic MHC class 1-restricted epitipe," Vaccine, 24: 1880-1888 (2006).
Menez-Jamet et al., "Optimized tumor cryptic peptides: the basis for universal neo-antigen-like tumor vaccines," Annals of Translational Medicine, 4: 266 (2016).
Vetsika et al., "Immunological responses in cancer patients after vaccination with the therapeutic telomerase-specific vaccine Vx-001," Cancer Immunology and Immunotherapy, 61: 157-168 (2011).
Malyguine et al., "Elispot Assay for Monitoring Cytotoxic T Lymphocytes (CTL) Activity in Cancer Vaccine Clinical Trials," Cells, 1: 111-126 (2012).
Georgoulias et al., "A multicenter randomized phase IIb efficacy study of Vx-001, a peptide-based cancer vaccine as maintenance treatment in advanced non-small-cell lung cancer: treatment rationale and protocol dynamics, " Clinical Lung Cancer, 14: 461-465 (2013).
International Search Report issued in corresponding International Patent Application No. PCT/EP2018/061602 dated Jul. 11, 2018.
Written Opinion issued in corresponding International Patent Application No. PCT/EP2018/061602 dated Jul. 11, 2018.

* cited by examiner

*Primary Examiner* — Anne Marie S Wehbe
(74) *Attorney, Agent, or Firm* — Arrigo, Lee, Guttman & Mouta-Bellum LLP (57) ABSTRACT

The invention pertains to the use of a tumor vaccine composed of two peptides of nine amino acids—the WT cryptic TERT572 (RLFFYRKSV, SEQ ID No: 1) expressed by tumor cells and its optimized variant TERT572Y (YLFFYRKSV, SEQ ID No: 2)—for treating cancer in a HLA-A*0201-positive patient having a non-immunogenic tumor expressing TERT.

12 Claims, 3 Drawing Sheets
Specification includes a Sequence Listing.

SEQUENCE LISTING

<160> NUMBER OF SEQ ID NOS: 9

<210> SEQ ID NO 1
<211> LENGTH: 9
<212> TYPE: PRT
<213> ORGANISM: Artificial Sequence
<220> FEATURE:
<223> OTHER INFORMATION: peptide from a human protein

<400> SEQUENCE: 1

Arg Leu Phe Phe Tyr Arg Lys Ser Val
1               5

<210> SEQ ID NO 2
<211> LENGTH: 9
<212> TYPE: PRT
<213> ORGANISM: Artificial Sequence
<220> FEATURE:
<223> OTHER INFORMATION: optimized peptide

<400> SEQUENCE: 2

Tyr Leu Phe Phe Tyr Arg Lys Ser Val
1               5

<210> SEQ ID NO 3
<211> LENGTH: 9
<212> TYPE: PRT
<213> ORGANISM: Artificial Sequence
<220> FEATURE:
<223> OTHER INFORMATION: peptide from a human protein

<400> SEQUENCE: 3

Ile Leu Ala Lys Phe Leu His Trp Leu
1               5

<210> SEQ ID NO 4
<211> LENGTH: 10
<212> TYPE: PRT
<213> ORGANISM: Artificial Sequence
<220> FEATURE:
<223> OTHER INFORMATION: peptide from a human protein

<400> SEQUENCE: 4

Asp Leu Gln Val Asn Ser Leu Gln Thr Val
1               5                   10

<210> SEQ ID NO 5
<211> LENGTH: 9
<212> TYPE: PRT
<213> ORGANISM: Artificial Sequence
<220> FEATURE:
<223> OTHER INFORMATION: peptide from a human protein

<400> SEQUENCE: 5

Leu Thr Leu Gly Glu Phe Leu Lys Leu
1               5

<210> SEQ ID NO 6
<211> LENGTH: 9
<212> TYPE: PRT
<213> ORGANISM: Artificial Sequence
<220> FEATURE:
<223> OTHER INFORMATION: peptide from a human protein

<400> SEQUENCE: 6

Ser Leu Leu Met Trp Ile Thr Gln Val
1               5

```
<210> SEQ ID NO 7
<211> LENGTH: 9
<212> TYPE: PRT
<213> ORGANISM: Artificial Sequence
<220> FEATURE:
<223> OTHER INFORMATION: peptide from a human protein

<400> SEQUENCE: 7

Thr Leu Glu Glu Ile Thr Gly Tyr Leu
1               5

<210> SEQ ID NO 8
<211> LENGTH: 9
<212> TYPE: PRT
<213> ORGANISM: Artificial Sequence
<220> FEATURE:
<223> OTHER INFORMATION: peptide from a human protein

<400> SEQUENCE: 8

Tyr Leu Glu Tyr Arg Gln Val Pro Asp
1               5

<210> SEQ ID NO 9
<211> LENGTH: 9
<212> TYPE: PRT
<213> ORGANISM: Artificial Sequence
<220> FEATURE:
<223> OTHER INFORMATION: peptide from a human protein

<400> SEQUENCE: 9

Tyr Leu Glu Tyr Arg Gln Val Pro Gly
1               5
```

USE OF A VACCINE TARGETING A CRYPTIC TERT EPITOPE, FOR TREATING CANCER IN A HLA-A*0201-POSITIVE PATIENT HAVING A NON-IMMUNOGENIC TUMOR EXPRESSING TERT

SEQUENCE LISTING SUBMISSION VIA EFS-WEB

A computer readable text file, entitled "SequenceListing.txt" created on or about Nov. 5, 2019 with a file size of about 3 kb contains the sequence listing for this application and is hereby incorporated by reference in its entirety.

FIELD OF THE INVENTION

The present invention pertains to the field of cancer immunotherapy, and more particularly to the field of antitumor vaccination.

BACKGROUND AND PRIOR ART

Cancer immunotherapy is intended to stimulate cytotoxic T lymphocytes (CTL) recognizing peptides derived from tumor antigens and presented at the tumor cell surface by HLA class I molecules. CTL-targeted peptides can be dominant or cryptic depending on their affinity for MHC molecules.

Tumor-associated antigens (TAA) are frequently expressed by both tumor cell and normal tissues, contrary to neoantigens that are tumor-specific and most often patient-specific. To circumvent the problem of tolerance to TAA while still targeting an antigen widely expressed by tumors, the inventors proposed a vaccine (Vx-001) targeting a cryptic peptide from TElomerase Reverse Transcriptase (TERT), i.e., a peptide that exhibits a low affinity for the HLA-A*0201 molecule and forms unstable peptide/HLA-I complexes (Menez-Jamet J. et al., 2016). Given the strong correlation between HLA-I affinity and immunogenicity, this cryptic peptide is naturally not immunogenic. To use it as a cancer vaccine, this cryptic peptide was hence optimized to enhance its immunogenicity.

Vx-001 is thus composed of two peptides of nine amino acids: the WT cryptic TERT572 (RLFFYRKSV, SEQ ID No: 1) expressed by tumor cells and its optimized variant TERT572Y (YLFFYRKSV, SEQ ID No: 2). These two peptides are administered separately, along with the adjuvant Montanide ISA51® VG (a mixture of a highly purified mineral oil (Drakeol 6VR) and a surfactant (Mannide monooleate). The optimized immunogenic TERT572Y is given in the first two vaccinations, in order to trigger a large immune response. The WT TERT572 is given in the following vaccinations, in order to select among all the TERT572Y stimulated T cells those with the highest specificity for the WT TERT572 that is presented on the surface of tumor cells associated with the HLA-A*0201.

Vx-001 was tested in a randomized phase IIb clinical trial in metastatic or recurrent stage I-III NSCLC patients who experienced disease control after four cycles of platinum-based chemotherapy. Patients needed to be HLA-A*0201 positive with a tumor expressing TERT. The primary objective of the study was overall survival. The result of this study was globally not statistically significant, but a detailed analysis of the results, taking into account analysis of patients specific immune response to the vaccine (immunomonitoring data), led to a stratification of the patients with identification of categories of patients for whom vaccination by Vx-001 proved beneficial.

The identification of tumor antigens was the first step on the way to tumor vaccination. Numerous tumor antigens were identified as targets of naturally activated antitumor T lymphocytes either in the blood or in the tumor (Tumor infiltrating lymphocytes, TILs). The idea was to use these antigens in order to amplify the naturally existing antitumor immune response. Speiser et al. proposed to add the existence of activated antigen-specific CD8 T cells as a further criterion for the selection of patients to vaccinate (Speiser D E. et al., 2003).

Similarly, Salazar et al. showed results demonstrating that patients who have pre-existent antigen-specific immune response detectable at the time of initiating vaccination achieve higher levels of tumor specific T cell immunity overall, most likely due to the boosting of the memory response. These authors thus suggested that developing vaccines targeting antigens that already demonstrate an increased incidence of endogenous immune responses in cancer patients may improve the vaccine potency and potentially therapeutic efficacy (Salazar L G. et al., 2007).

In another publication, the authors stated that the overall prevalence of these endogenous responses would be informative to optimize further peptide vaccination clinical trial (Cesson V. et al., 2011).

The widely accepted idea was therefore to use cancer vaccines in order to amplify a pre-existing antitumor immune response.

However, in numerous clinical trials, a very weak correlation between vaccine-induced immune response and clinical response was observed. For instance, a strong immune response was not always followed by a strong clinical response. Moreover, in most responding patients, a very low number of vaccine-induced T cells were observed in the blood, while in regressing tumors, an important expansion of antitumor T cells against antigens other than the vaccine itself were detected. These observations led to a new hypothesis about the mechanism of action of cancer vaccines (Ma W. et al, 2011, Coulie P G. et al. 2014). According to this hypothesis, a small number of active anti-vaccine T cells penetrate a tumor and attack tumor cells. As a result of this interaction, these CTL are restimulated and produce cytokines that reverse the local microenvironment. This reawakens many of the inactive antitumor T cells that are already present in the tumor. The mobilization of these T cells—which are directed against tumor antigens other than the vaccine antigen—provides the numbers that are required to reject the tumor.

According to this hypothesis, tumor vaccines may have an antitumor clinical activity only in patients with immunogenic tumors able to stimulate a polyspecific endogenous antitumor immune response.

Amongst non small cell lung cancer patients, this population with immunogenic tumors corresponds to those with the better prognosis. Indeed, the high densities of CD4+ and CD8+ T Infiltrating Lymphocytes (TILs), associated to a high mutational burden in the tumor stroma was shown to be an indicator of good prognosis in NSCLC patients (Al-Shibli K I. et al., 2008) and in other tumors (Fridman W H. et al. 2011). This observation led to the development of methods to score patients prognosis based on TILs analysis as with immunoscore (Pagès F. et al. 2009) or to identify molecular signatures associated with the immunological status of the tumor and prognosis for response to immunotherapy (Wang E. et al. 2013).

Moreover, immune checkpoint inhibitors that have enhanced the field of immunotherapy during the last years and have obtained market authorizations for several cancer indications were shown to be efficient only in patients in whom tumors have a high somatic nonsynonymous mutation burden (Soo R A. 2015) associated to a strong infiltration by TILs (Fehrenbacher L. et al., 2016). Finally, good prognosis, immune checkpoint inhibitors efficacy and high mutational burden associated to immunogenic tumors were shown to be all strongly associated with a molecular signature identified in smoker patients, whereas never-smokers or light former smokers were shown to have a poor benefit from immune checkpoint inhibitor treatment (Rizvi N A. et al., 2015).

SUMMARY OF THE INVENTION

The invention relates to the selection of patients more likely to respond to vaccination by Vx-001, a vaccine composed of two peptides (SEQ ID No:1 and SEQ ID No: 2) administered separately.

Contrary to what would have been expected from the prior art, the fine analysis of the Vx-001 phase IIb clinical trial showed that the patients who better benefited from the treatment were those with the worst prognosis, who had no pre-existent tumor specific immune response detectable at the time of initiating vaccination (i.e., patients having a non-immunogenic or a poorly immunogenic tumor).

The invention thus pertains to the use of this vaccine and of each of its components, for treating cancer in a HLA-A*0201-positive patient having a non-immunogenic tumor expressing TERT.

The invention also pertains to a theranostic method to determine whether a HLA-A*0201-positive patient having a tumor expressing TERT is likely to respond to Vx-001, wherein the patient is likely to be a good responder if the tumor is non-immunogenic.

Another aspect of the present invention is a kit to perform the theranostic method.

DETAILED DESCRIPTION OF THE PREFERRED EMBODIMENTS

According to a first embodiment, the present invention pertains to the use of the optimized peptide TERT572Y (peptide of SEQ ID No: 2), for inducing an anti-tumor CTL response in an HLA-A*0201-positive patient having a non-immunogenic tumor expressing TERT.

When performing this anticancer immunotherapy, vaccination with TERT572Y induces a CTL response against the cryptic peptide TERT572 (SEQ ID No: 1). The CTL response induced by the initial vaccination with the peptide of SEQ ID No: 2 is then preferably maintained (or amplified) by vaccination with the peptide of SEQ ID No:1.

In the present text, an "immunogenic tumor" designates a tumor that elicits a significant CTL response against tumor antigens. When performing the present invention, the immunogenicity of the tumor can be assessed by measuring, in a blood sample from the patient, the number of CTLs specific for TERT572 (SEQ ID No: 1) and/or the number of CTLs specific for TERT540 (SEQ ID No: 3), and/or the number of CTLs specific for another tumor antigen. For example, the immunogenicity of the tumor can be assessed by measuring the CTL response against Survivin, which is a universal tumor antigen expressed by a large majority of tumors (Andersen M H. and Thor S P., 2002). In HLA-A*0201-positive patients considered herein, this response can be detected by measuring, in a blood sample from the patient, the number of CTLs specific for the epitope Survivin96 (SEQ ID No: 5).

A contrario, the tumor will be considered as "non-immunogenic" if no CTL response specific for TERT572 (SEQ ID No: 1), TERT540 (SEQ ID No: 3) and/or Survivin96 (SEQ ID No: 5) is detected in a blood sample from the patient. The IFNg ELISpot assay described in the experimental part below can be used to detect T cells specific for the TERT572 peptide or for any other tumor epitope. Of course, as described in the experimental part below, in absence of a significant difference between the response to the tumor antigen tested peptide and the response to an irrelevant peptide, it will be considered that there is no response specific for the tested tumor peptide, i.e., that the tumor is non-immunogenic.

Alternatively, the immunogenicity of the tumor can be assessed by measuring the level of tumor-infiltrating lymphocytes (TILs) in a biopsy from the tumor such as with immunoscore (Pages F. et al. 2009) or determining the profile of genes expression of the tumor using gene profiling methods (Galon J. at al., 2013, Rizvi N A. et al., 2015, Wang E. et al. 2013).

As used herein, "cancer" means all types of cancers. In particular, the cancers can be solid or hematopoietic cancers. Non limitative examples of cancers are squamous carcinomas or adenocarcinomas such as breast, prostate, ovary, lung, pancreas or colon cancer, sarcomas, lymphomas, melanomas, leukemias, germ cell cancers and blastomas.

As used herein, the terms "treat", "treatment" and "treating" refer to any delay of the progression, reduction of severity, and/or duration of cancer, particularly a solid tumor; for example, in a non-small cell lung cancer (NSCLC), amelioration of quality of life thereof and/or an increase in survival that results from the administration of one or more therapies.

The present invention also pertains to the use of the native peptide TERT572 (peptide of SEQ ID No: 1), for treating cancer in an HLA-A*0201-positive patient having a non-immunogenic tumor expressing TERT. In the frame of this immunotherapy treatment, the peptide of SEQ ID No: 1 maintains a CTL immune response initiated by vaccination of the patient with a peptide of SEQ ID No: 2.

The present invention also relates to the use of Vx-001, i.e., the combination of peptides of SEQ ID No: 1 and SEQ ID No: 2, in the treatment of cancer in an HLA-A*0201-positive patient having a non-immunogenic tumor expressing TERT. As already described, the two peptides of Vx-001 are administered separately. A CTL response against the tumor antigen TERT, more precisely against the cryptic TERT peptide of SEQ ID No: 1 is first induced by vaccinating the patient with the peptide of SEQ ID No: 2 and then maintained by vaccinating the patient with the peptide of SEQ ID No: 1.

According to a preferred embodiment illustrated in the experimental part below, the patient first receives 2 vaccinations with the peptide of SEQ ID No: 2 and then 4 vaccinations with the peptide of SEQ ID No:1, with a three weeks interval between said vaccinations ("inducing phase"). Of course, the skilled artisan (physician or clinical investigator) can chose a different vaccination protocol. Possible variations include the number of initial vaccinations with SEQ ID No: 2 (one, two or more) for inducing the CTL response, the interval between the vaccinations (for example, from 1 to 4 weeks or more), the number of vaccinations with SEQ ID No: 1 in this inducing phase (from 1 to 10 or more), and the formulation of the vaccine. In particular, adjuvants different from Montanide can be tested and could possibly necessitate an adaptation of the protocol.

According to another embodiment, after the inducing phase mentioned above, the patient receives additional vaccinations with the peptide of SEQ ID No:1, to maintain the CTL response against TERT ("stabilization phase"). These additional vaccinations can for example be administered every 3 months. They can be administered until relapse. Of course, the skilled artisan (physician or clinical investigator) can chose a different protocol for the stabilization phase. Possible variations include those concerning the interval between the vaccinations (for example, vaccinations can be performed every month, every 2 months, or less frequently, for example every 6 months, especially after a long period of remission), as well as the peptide used. Indeed, the clinician can choose to monitor the CTL response regularly and vaccine the patient with the peptide of SEQ ID No: 2 again if a decrease in the response is observed. In other words, the clinician can adapt the stabilization phase depending on the patient's response and status.

The inventors found that in some patients, a CTL response against tumor antigens is detected after chemotherapy and before vaccination, probably because tumor cell lysis following chemotherapy leads to the release of a large amount of tumor epitopes able to induce an antitumor immune response in these patients. These tumor specific CTLs are highly detectable just after the end of chemotherapy, and the amount of CTLs then decreases in the following weeks. The inventors' hypothesis is that this CTL response appears in patients having an immunogenic tumor, who are those who are fully responsive to other immunotherapies such as anti-PD(L)1 treatment. Therefore, for patients who received a chemotherapy treatment such as a platinum-based first line chemotherapy, the immunogenicity status of the tumor will preferably be assessed less than 2 weeks after the end of said chemotherapy, for example less than 7 days after the end of the chemotherapy.

According to a particular embodiment of the present invention, the tumor is considered as non-immunogenic if no CTL response specific for TERT572 (SEQ ID No: 1) is detectable in a blood sample from the patient collected before vaccination and preferably less than 2 weeks after the end of a platinum-based first line chemotherapy, more preferably less than 7 days after the end of a platinum-based first line chemotherapy.

According to another particular embodiment of the present invention, the tumor is considered as non-immunogenic if no CTL response specific for TERT540 (SEQ ID No: 3) is detectable in a blood sample from the patient collected before vaccination and preferably less than 2 weeks after the end of a platinum-based first line chemotherapy, more preferably less than 7 days after the end of a platinum-based first line chemotherapy.

According to another particular embodiment of the present invention, the tumor is considered as non-immunogenic if no CTL response specific for Survivin96 (SEQ ID No: 5) is detectable in a blood sample from the patient collected before vaccination and preferably less than 2 weeks after the end of a platinum-based first line chemotherapy, more preferably less than 7 days after the end of a platinum-based first line chemotherapy.

According to another particular embodiment of the present invention, illustrated in the experimental part below, the patient has a non small cell lung cancer (NSCLC).

As shown in the results of the phase IIb study disclosed below, vaccination with Vx-001 significantly prolonged survival in patients with non-immunogenic non-squamous NSCLC. Hence, according to another particular embodiment of the present invention, the patient has a non-squamous (NSQ) NSCLC.

The results of the clinical trial also show that never-smokers and former smokers who have been smoking during less than 30 years respond better to the treatment.

Hence, according to another particular embodiment of the present invention, the patient is a never-smoker or is a former smoker who smoked during less than 30 years.

According to another preferred embodiment of the present invention, the patient is a never-smoker or is a former smoker who smoked during less than 25 years.

According to another preferred embodiment of the present invention, the patient is a never-smoker or is a former smoker who smoked during less than 20 years.

According to another preferred embodiment of the present invention, the patient is a never-smoker or is a former smoker who smoked during less than 10 years.

Surprisingly, the inventors observed even more statistically significant results when the light-smokers (i.e., individuals who smoke during at most 25 years), including patients who did not stop smoking but started less than 25 years or cumulated less than 25 years smoking in their life, were selected. Hence, according to yet another preferred embodiment of the present invention, the patient is a never-smoker or a light-smoker.

According to another particular embodiment of the present invention, illustrated in the experimental part below, the patient has received a platinum-based chemotherapy prior to vaccination with Vx-001, in particular prior to administration of the peptide of SEQ ID No: 2.

According to another particular embodiment of the present invention, the patient responded (objective response and stable disease) to a platinum-based first line chemotherapy prior to the first vaccination with the peptide of SEQ ID No: 2.

According to a more particular embodiment of the present invention, illustrated in the experimental part below, the patient has received a cisplatin-based chemotherapy (CDDP) prior to vaccination with Vx-001, in particular prior to administration of the peptide of SEQ ID No: 2.

According to another more particular embodiment of the present invention, the patient responded (objective response and stable disease) to a cisplatin-based first line chemotherapy prior to the first vaccination with the peptide of SEQ ID No: 2.

Other therapeutic schemes are envisioned in the frame of the present invention. For example, Vx-001 can be administered in an HLA-A*0201-positive patient having a non-immunogenic tumor expressing TERT either before or during chemotherapy. In this case, immunogenic status of the tumor will be determined before chemotherapy. First-line Vx-001 treatment can also be envisioned for HLA-A*0201-positive patients having a non-immunogenic tumor expressing TERT, especially if they are never-smokers of former smokers who smoked for less than 30 years or light-smokers (individuals who have smoked during less than 25 years and who stopped smoking or not). In this case, immunogenic status of the tumor will be determined at diagnosis. In any case, immunogenic status of the tumor will be determined either by detecting tumor antigen specific CTLs using enzyme-linked immunospot (ELISpot) IFNg assay or by any other method such as TILs detection or gene expression profiling.

According to another particular embodiment of the present invention, the patient is more than 65 years old. The results of the clinical trial indeed show that patients more than 65 years old respond better to the treatment.

According to another particular embodiment of the present invention, the patient is a male. The results of the clinical trial indeed show that male patients respond better to the treatment.

Another aspect of the present invention is a method for in vitro determining whether an HLA-A*0201-positive patient having a tumor expressing TERT is likely to be a good responder to an immunotherapy treatment by vaccination with Vx-001, comprising measuring the immunogenicity of the tumor; the patient is considered as a good candidate for Vx-001 vaccination if the tumor is non-immunogenic.

According to a particular embodiment of the above method, the tumor immunogenicity of the tumor is assessed by measuring CTL response specific for the peptide of SEQ ID No: 1 in a blood sample from said individual, wherein if no such CTL response is detectable before vaccination, the tumor is considered non-immunogenic.

According to another particular embodiment of the above method, the immunogenicity of the tumor is assessed by measuring CTL response specific for the peptide of SEQ ID No: 3 in a blood sample from said individual, wherein if no such CTL response is detectable before vaccination, the tumor is considered non-immunogenic.

According to yet another particular embodiment of the above method, the immunogenicity of the tumor is assessed by measuring CTL response specific for the peptide of SEQ ID No: 5 in a blood sample from said individual, wherein if no such CTL response is detectable before vaccination, the tumor is considered non-immunogenic.

According to a particular embodiment of the method according to the invention, CTL response specific for the peptide of SEQ ID No: 1 or for the peptide of SEQ ID No: 3 or for the peptide of SEQ ID No: 5 or for any other relevant tumor-specific peptide is detected by enzyme-linked immunospot (ELISpot) IFNg assay.

As mentioned above, the correlation between natural immunity and immunogenicity is higher when natural immunity is assessed close to the end of chemotherapy. According to another particular embodiment of the method according to the invention, the immunogenicity of the tumor is thus assessed less than two weeks, preferably less than 7 days after the end of chemotherapy.

Of course, when performing the theranostic method according to the invention, any other method can be used for assessing the immunogenicity of the tumor. In particular, this can be done by measuring the amount of TILs in a biopsy from the tumor or by gene profiling.

The present invention also pertains to a kit of parts for performing the theranostic method described above, comprising (i) reagents and a plate for performing an ELISpot assay, (ii) a peptide selected amongst SEQ ID No: 1, SEQ ID No: 3 and SEQ ID No: 5 and (iii) an irrelevant peptide as negative control.

Other characteristics of the invention will also become apparent in the course of the description which follows of the clinical study and biological assays which have been performed in the framework of the invention and which provide it with the required experimental support, without limiting its scope.

EXPERIMENTAL RESULTS

Material and Methods
Study Design and Participants

The Vx-001-201 study is a randomized, double blind multicenter study done in 70 centers in France, Germany, Spain, Italy, Greece, Poland, Romania and Czech Republic. Key eligibility criteria were a) non small cell lung cancer (NSCLC), b) stage IV or recurrent stage I-III, c) disease control after platinum based first line chemotherapy according to RECIST 1.1 criteria, d) HLA-A*0201 positivity, e) tumors expressing TElomerase Reverse Transcriptase (TERT), f) ECOG 0 or 1 g) absence of brain metastasis.

The study was conducted according to the Declaration of Helsinki and all applicable regulatory and ethical requirements. The study was approved by the Independent Ethics Committee responsible for each study site in accordance with the local legislation. All patients provided written informed consent.

Endpoints
a) Principal endpoint: overall survival (OS) measured from randomization
b) Secondary endpoints:
Time to Treatment Failure (TTF) measured from randomization
OS at 12 months
c) Main exploratory objectives
Evaluation of vaccine induced specific immune response
Correlation between vaccine specific immune response and clinical response Procedures and Vaccination Protocol Patients who fulfilled all inclusion criteria were randomized within 4 weeks after the end of first line chemotherapy.

Figure 1:
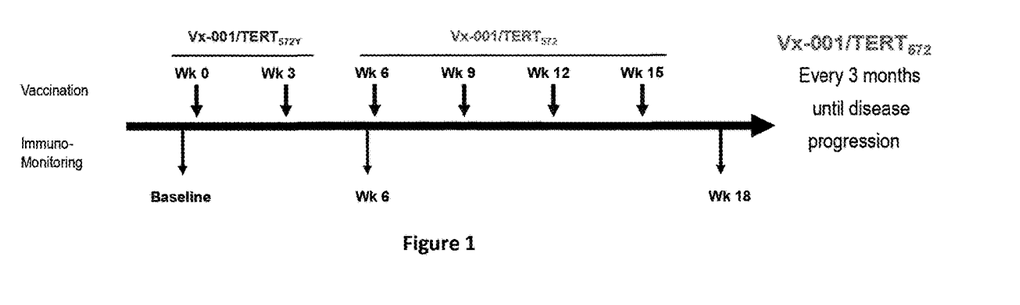
FIG. 1: Vaccination protocol

The vaccination protocol consisted in six vaccinations at three week interval. The optimized Vx-001/TERT572Y was used in the first two vaccinations and the native Vx-001/TERT572 in the following four vaccinations. Patients who continued controlling their disease after the sixth vaccination received boost vaccination with the Vx-001/TERT572 every three months. Vaccination was stopped at disease progression (FIG. 1).

Immune response was evaluated before the first vaccination (baseline), before the third vaccination (W6) and three weeks after the sixth vaccination (W18). Patients who received boost vaccinations were monitored for immune response every six months.

Statistical Analysis

To calculate the sample size we estimated the median OS of the placebo arm to be 9.8 months and we expected the median OS in the Vx-001 arm to be 15.2 months. Thus, we needed to randomize 220 patients (including 10% of drop out at the final analysis) to achieve a power of 83% and a one-sided alpha of 0.05.

The placebo: Vx-001 ratio was 1:1.

The primary and secondary endpoints were analysed in the Full Analysis Set (FAS) composed of all patients who fulfilled the five main criteria a) NSCLC, b) stage IV or recurrent stage I-III, c) disease control after first line chemotherapy, d) HLA-A*0201 positivity and e) TERT expressing tumors.

We used the Kaplan-Meier method to estimate OS and TTF in each arm and a Cox proportional hazards regression model to estimate Hazard Ratio (HR) relating OS and TTF to the treatment effect.

Immunomonitoring

Immune response was measured using IFNg ELISpot assay to detect T cells specific for the TERT572 peptide. Peripheral Blood Mononuclear Cells (PBMC) were isolated from blood samples collected before vaccination, at W6 (before the third vaccination), W18 (three weeks after the $6^{th}$ vaccination) and every six months thereafter for patients who received boost vaccinations. PBMC were stored at $-160°$ C. and tested when study was unblended. $2\times10^5$ PBMC/well were overnight stimulated with TERT572 or an irrelevant peptide as negative control or the CEF peptides pool as positive control or Phyto hemagglutinin (PHA) as a specific positive control in plates coated with anti IFNg antibody (Diaclone) in AIMV serum free medium (in 6-plicate). The presence of alive PBMC was verified using PHA. The quality of the PBMC was evaluated by measuring the response to CEF peptides pool (a mixture of polyallelic epitopic peptides from common viruses, flu, HPV and CMV). Samples were considered when they responded to CEF or when all samples from the same patient were unresponsive to CEF (indicating an absence of CEF reactivity due to patient medical history). Number of spots were quantified using a counter and for each condition, the average of the 6 values was calculated. A blood sample was considered responsive to TERT572 or CEF when a) there was a difference higher than 10 spots between the negative control average value and the TERT572 or CEF group average value and b) there was a statistically significant difference between negative control average value and TERT572 or CEF group average value ($p<0.05$). A patient without pre-vaccination TERT572 response was considered immune responder when a response to TERT572 was detected during the study protocol. Patients with pre-vaccination TERT572 reactivity were considered as immune responders only if (i) this TERT572 reactivity was amplified (at least two folds) after vaccination or if (ii) the patient first lost the pre-vaccination TERT572 reactivity and a new TERT572 reactivity was detected later in the vaccination protocol.

Immune responses to other TERT peptides and to other antigens were also measured using IFNg ELISpot assay. The peptides used to detect T cells are described in Table 1 below.

TABLE 1

| peptides used to detect specific CTLs | | | |
|---|---|---|---|
| Antigen | Peptide | Sequence | SEQ ID No |
| TERT | TERT 540 | ILAKFLHWL | 3 |
| TERT | TERT 988 | DLQVNSLQTV | 4 |
| Survivin | Survivin-3A 96 | LTLGEFLKL | 5 |
| NY-ESO-1 | NY-ESO-1 157 | SLLMWITQV | 6 |
| HER-2/neu | HER-2/neu402 | TLEEITGYL | 7 |
| MAGE-A | MAGE-A248D9 | YLEYRQVPD | 8 |
| MAGE-A | MAGE-A24809 | YLEYRQVPG | 9 |

Results

Patients 1407 patients were screened and 221 patients were randomized. The main reasons for screening failure were a) patients were HLA-A*0201 negative, b) there was no biopsy material suitable for TERT expression evaluation and c) disease progressed after first line chemotherapy.

Thirty-one patients were excluded from the Full Analysis Set (FAS) analysis because they did not fulfil the main inclusion criteria (25 patients entered the study with progressive disease, 2 patients with a tumor other than NSCLC and 4 patients with no metastatic or recurrent disease). Table 2 shows demographics of the 190 patients of the FAS.

TABLE 2

| Demographics of evaluated patients. | | | | |
|---|---|---|---|---|
| All patients | Placebo 101 | | Vx-001 89 | |
| Sex | | | | |
| Male | 72 | 71% | 60 | 67% |
| Female | 29 | 29% | 29 | 33% |
| Age | | | | |
| >65 years | 54 | 54% | 45 | 50% |
| <65 years | 47 | 46% | 44 | 50% |
| Histology | | | | |
| NSQ | 59 | 59% | 55 | 62% |
| SQ | 38 | 37% | 34 | 38% |
| Mixt | 4 | 4% | | |
| Response to 1st line chemotherapy | | | | |
| OR | 52 | 52% | 36 | 40% |
| SD | 49 | 48% | 53 | 60% |
| ECOG | | | | |
| 0 | 42 | 42% | 33 | 37% |
| 1 | 59 | 58% | 56 | 63% |
| Stage | | | | |
| IV | 89 | 89% | 73 | 82% |
| recurrent | 12 | 11% | 16 | 18% |
| Smoking status | | | | |
| Never smoker | 15 | 15% | 10 | 11% |
| Former smoker (all) | 52 | 51% | 63 | 71% |
| Former smoker (smoker during ≤20 years) | 10 | 10% | 12 | 13% |
| Former smoker (smoker during ≤25 years) | 14 | 14% | 16 | 18% |
| Former smoker (smoker during <30 years) | 17 | 17% | 19 | 21% |

TABLE 2-continued

Demographics of evaluated patients.

|  | Placebo 101 |  | Vx-001 89 |  |
|---|---|---|---|---|
| All patients |  |  |  |  |
| Former smoker (smoked during >30 years) | 35 | 35% | 44 | 49% |
| Current smoker | 34 | 34% | 16 | 18% |

NSQ: non-squamous.
SQ: squamous.
OR: objective response.
SD: stable disease
ECOG: Eastern Cooperative Oncology Group scale of performance status.

Patients were randomized within 4 weeks after the end of chemotherapy.

Immune Response in FAS Patients

TERT572 specific immune response was detected before vaccination (natural immunity) in 45 out of 166 evaluable patients (27.1%). Percentage of patients with natural immunity was 24.1% and 30.4% in placebo-treated and Vx-001-treated patients respectively.

Figure 2:
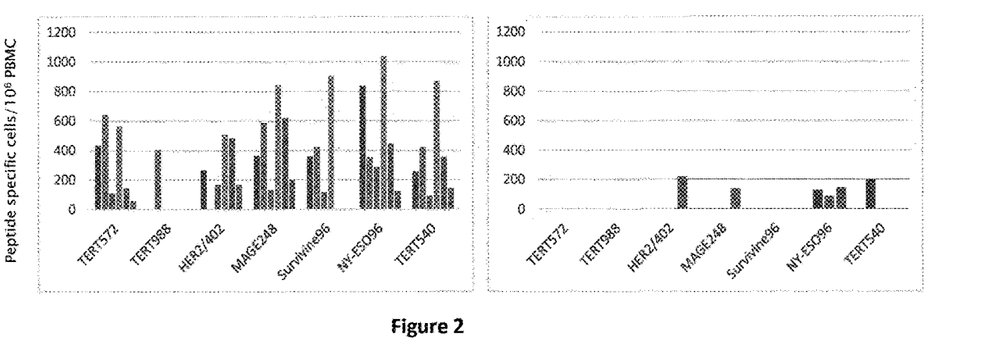
FIG. 2: Response to different tumor antigens of patients with (left) or without (right) natural immunity

Natural immunity was not limited to TERT572 but extended to other tumor antigens. Blood samples of baseline of six patients with natural immunity and three patients without natural immunity were tested against six additional antigens overexpressed in NSCLC. All patients with natural immunity to TERT572 had T cells reactive to other tumor antigens (such as TERT988, TERT540, MAGE248, HER402, Survivin96, NY-E5096) while patients without natural immunity to TERT572 did not respond to other tumor antigens and in the rare case a response was detected, it was very weak (FIG. 2).

These results strongly suggest that patient with natural immunity against TERT572 have immunogenic tumors while patients without natural immunity against TERT572 have non-immunogenic or poorly immunogenic tumors.

In Vx-001 treated patients, TERT572 specific immune response was evaluated in 79 patients at baseline, 73 patients at W6, 42 patients at W18 and 16 patients who received boost vaccinations. Overall, immune response was measured at least at W6, W18 or thereafter in 75 patients.

Twenty-two patients mounted a TERT572 specific immune response (29.3%). Surprisingly this response was significantly more frequent in non-squamous (NSQ) than in squamous (SQ) NSCLC (36% vs 13.3%, p=0.037).

The frequency of patients with vaccine-induced immune response was not significantly different between patients with and patients without natural immunity against TERT572 (15% vs 36.2% p=0.14).

Clinical Response

Figure 3:
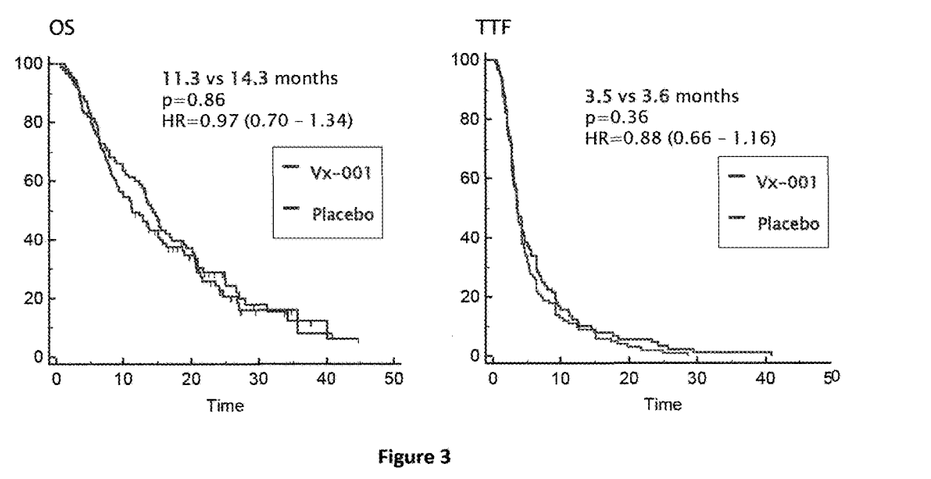
FIG. 3: Clinical outcome (OS and TTF) of all evaluated patients

Analysis of the FAS patients showed that there was no significant difference in OS between placebo treated and Vx-001 treated patients (11.3 vs 14.3 months, p=0.86, HR=0.97, 95% CI 0.70-1.34). There was significant difference neither in TTF (3.5 vs 3.6 months, p=0.36, HR=0.88, 95% CI 0.66-1.16) nor in 12 months survival (49.5% vs 58%, p=0.24) (FIG. 3).

Subgroups analysis showed no significant difference in OS and 12 months survival (table 3) in either subgroup tested excepted the 12 months survival that was significantly higher in males (43% vs 61%, p=0.05).

TABLE 3

Sub-group analysis for OS and 12 months survival

| Sub-group | Median survival (months) | | P value | HR | 95% CI | 12 months OS (%) | | P value |
|---|---|---|---|---|---|---|---|---|
|  | Placebo | Vx-001 |  |  |  | Placebo | Vx-001 |  |
| Histology |  |  |  |  |  |  |  |  |
| NSQ (n = 118) | 11.3 | 13.4 | 0.56 | 0.88 | 0.58-1.34 | 50 | 55 | 0.58 |
| SQ (n = 72) | 11.2 | 14.3 | 0.64 | 1.13 | 0.66-1.93 | 46 | 64 | 0.16 |
| Response to chemotherapy |  |  |  |  |  |  |  |  |
| OR (n = 87) | 11.1 | 15.3 | 0.64 | 0.89 | 0.54-1.45 | 48 | 69 | 0.07 |
| SD (n = 103) | 12.4 | 14.3 | 0.98 | 0.99 | 0.64-1.55 | 51 | 52 | 1 |
| 1st line chemotherapy |  |  |  |  |  |  |  |  |
| CARBO (n = 119) | 12.8 | 14.3 | 0.76 | 1.06 | 0.69-1.63 | 50 | 58.2 | 0.46 |
| CDDP (n = 69) | 9.9 | 15 | 0.44 | 0.81 | 0.48-1.32 | 46 | 59 | 0.33 |
| Age |  |  |  |  |  |  |  |  |
| >65 years (n = 98) | 10 | 15 | 0.29 | 0.78 | 0.50-1.24 | 42.6 | 59 | 0.11 |
| <65 years (n = 92) | 15.4 | 13.4 | 0.36 | 1.2 | 0.77-2.00 | 55.3 | 57.7 | 0.83 |
| Sex |  |  |  |  |  |  |  |  |
| Male (n = 131) | 9.9 | 15 | 0.29 | 0.81 | 0.55-1.20 | 43 | 61 | 0.05 |
| Female (n = 59) | 15.8 | 13.2 | 0.16 | 1.52 | 0.82-2.79 | 62 | 53.3 | 0.6 |

Figure 4:
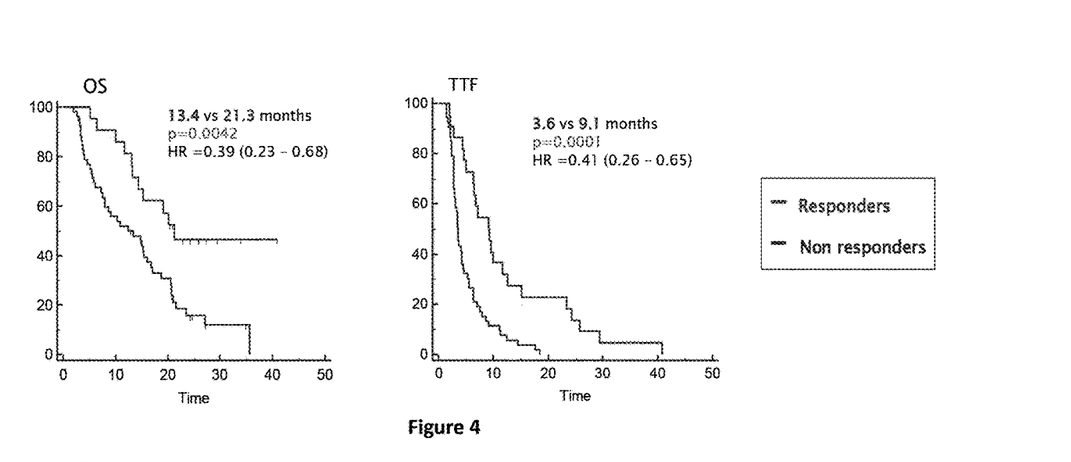
FIG. 4: Clinical outcome (OS and TTF) of Vx-001 treated patients who developed a vaccine specific immune response

We then asked whether there is a correlation between the Vx-001 induced immune response and clinical outcome and we compared OS and TTF between Vx-001 responders and Vx-001 non-responders vaccinated patients. There was a very significant difference in OS (13.4 vs 21.3 months, p=0.0042, HR=0.39, 95% CI 0.23-0.68) and TTF (3.6 vs 9.1 months, p=0.0001, HR=0.41, 95% CI 0.26-0.45) (FIG. 4).

We then analyzed the impact of natural immunity on OS, TTF and 12 months survival in placebo and Vx-001 treated patients, considered separately. Tables 4 and 5 show that in the placebo-treated population, natural immunity was related to a quite significant prolongation of OS (8.6 vs 20.1 months, p=0.057, HR=0.59, 95% CI 0.36-0.98) and TTF (3.1 vs 5.3 months, p=0.056, HR=0.63, 95% CI 0.40-0.98). The difference in 12 months survival was statistically significant (71.4% vs 36.3%, p=0.006).

In contrast, in Vx-001 treated patients, there was no difference in OS (13.2 vs 15.5 months, 0.73, HR=0.91 95% CI 0.53-1.54) and TTF (4.1 vs 2.9 months, p=0.16, HR=1.4, 95% CI 0.83-2.33). There was no significant difference in 12 months survival either (55% vs. 65%, p=0.46).

TABLE 4

Clinical outcome of placebo and Vx-001 treated patients with and without natural immunity (OS)

| Sub-group | Median survival (months) | | P value | HR | 95% CI | 12 months OS % | | P value |
|---|---|---|---|---|---|---|---|---|
| | No natural immunity (n = 122) | Natural immunity (n = 45) | | | | No natural immunity | Natural immunity | |
| Placebo treated (n = 87) | 8.6 | 21 | 0.057 | 0.59 | 0.36-0.98 | 36.3 | 71.4 | 0.006 |
| Vx-001 treated (n = 80) | 13.2 | 15.5 | 0.73 | 0.91 | 0.53-1.54 | 55 | 65 | 0.46 |

TABLE 5

Clinical outcome of placebo and Vx-001 treated patients with and without natural immunity (TTF)

| Sub-group | Median survival (months) | | P value | HR | 95% CI |
|---|---|---|---|---|---|
| | No natural immunity (n = 122) | Natural immunity (n = 45) | | | |
| Placebo treated (n = 87) | 3.1 | 5.3 | 0.056 | 0.63 | 0.40-0.98 |
| Vx-001 treated (n = 80) | 4.1 | 2.9 | 1.4 | 0.83 | 0.53-2.33 |

These results show that patients with immunogenic tumors have a better clinical outcome than patients with non-immunogenic tumors. Importantly, this difference in clinical outcome between immunogenic and non-immunogenic tumors disappeared in patients treated with Vx-001. In other words, Vx-001 treated patients with non-immunogenic tumors had the same clinical outcome as patients with immunogenic tumors.

These results led us to focus our attention on patients with non-immunogenic tumors. Table 6 shows demographic data of the population of patients without natural immunity against TERT572. There is no imbalance between placebo and Vx-001-treated patients in terms of histology, response to first-line chemotherapy, first-line chemotherapy, gender, age and smoking history.

TABLE 6

Demographics of patients without natural immunity

| All patients | Placebo 66 | | Vx001 56 | |
|---|---|---|---|---|
| Sex | | | | |
| Male | 50 | 76% | 39 | 70% |
| Female | 16 | 24% | 17 | 30% |

TABLE 6-continued

Demographics of patients without natural immunity

| All patients | Placebo 66 | | Vx001 56 | |
|---|---|---|---|---|
| Age | | | | |
| >65 years | 35 | 53% | 28 | 50% |
| <65 years | 31 | 47% | 28 | 50% |
| Histology | | | | |
| NSQ | 37 | 56% | 37 | 66% |
| SQ | 27 | 41% | 19 | 34% |
| Mixt | 2 | 3% | | |
| Response to 1st line chemotherapy | | | | |
| OR | 36 | 55% | 19 | 34% |
| SD | 30 | 45% | 37 | 66% |
| 1st line chemotherapy | | | | |
| CARBO | 42 | 64% | 32 | 57% |
| CDDP | 24 | 36% | 22 | 39% |
| CARBO/CDDP | | | 2 | |
| Stage | | | | |
| IV | 60 | 91% | 47 | 84% |
| recurrent | 6 | 9% | 9 | 16% |
| Smoking status | | | | |
| Never smoker | 7 | 11% | 7 | 13% |
| Former smoker (all) | 33 | 50% | 39 | 70% |
| Former smoker (≤20 years) | 5 | 8% | 8 | 14% |
| Former smoker (≤25 years) | 9 | 14% | 10 | 18% |
| Former smoker (<30 years) | 11 | 17% | 11 | 20% |
| Current smoker, including 5 light-smokers (≤25 years) | 26 | 39% | 10 | 18% |

Figure 5:
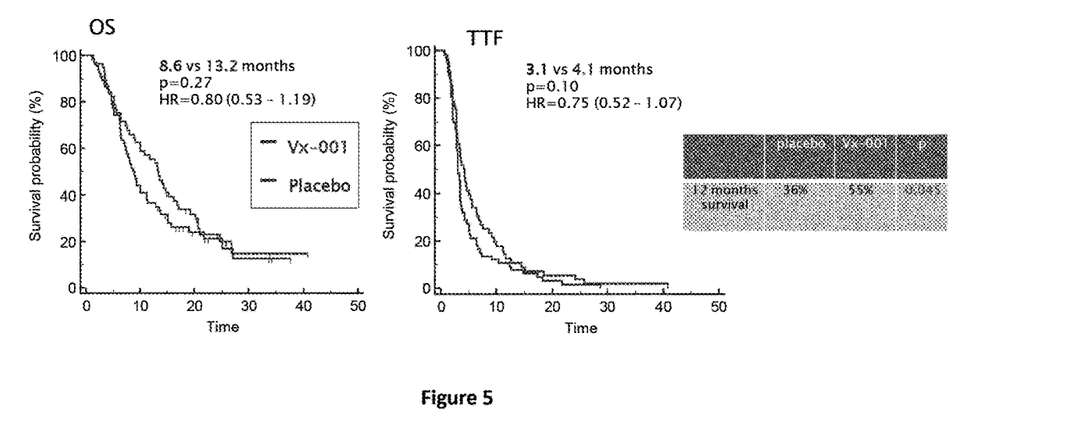
FIG. 5: Clinical outcome of patients without natural immunity

There is not a significant difference in OS between these two groups (8.6 vs 13.2 months, p=0.27, HR=0.80 95% CI 0.53-1.9) but a positive trend in TTF (3.1 vs 4.1 months, p=0.10, HR=0.75, 95% CI 0.52-1.07) and a significant difference in 12 months survival (55% vs 36%, p=0.045) (FIG. 5). These differences were increased when natural immunity was assessed less than 26 days after the end of chemotherapy in OS (6.5 vs 11.7 months, p=0.04, HR=0.58 95% CI 0.33-1.0 and TTF (3 vs 4.1 months, p=0.05, HR=0.62 95% CI 0.36-1.0) whereas no significant difference was observed in patients for whom natural immunity was assessed later than 26 days after chemotherapy (OS 10 vs 13.2 months, p=0.91, HR=0.96 95% CI 0.54-1.78) (n.b.: 26 days is the median of the period between the end of chemotherapy and randomization of a patient (inclusion in a group) in our cohort).

Figure 6:
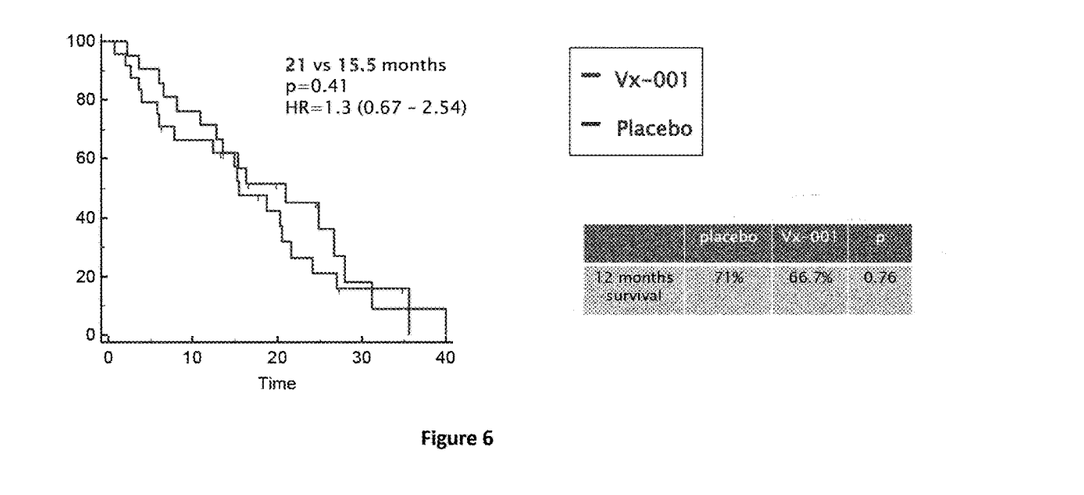
FIG. 6: Clinical outcome of patients with natural immunity

In contrast, there was no difference in OS and 12 months survival between placebo and Vx-001-treated patients with natural immunity (FIG. 6) even if the tumor immunogenicity was assessed before 26 days after the end of chemotherapy (OS (21 vs 15.3 months, p=0.31, HR=1.54 95% CI 0.61-3.88) and TTF (5.4 vs 2.2 months, p=0.08, HR=1.98 95% CI 0.82-4.79)).

Analysis of different sub-groups showed that Vx-001 significantly prolonged survival in patients with non-immunogenic NSQ tumors (7.7 vs 13.4 months, p=0.034, HR=0.58, 95% CI 0.35-0.97) and in patients with non-immunogenic tumors having been treated with cisplatin-based (CDDP) chemotherapy (7.1 vs 13.4 months, p=0.032, HR=0.51, 95% CI 0.26-0.98). Moreover, there was a significant difference in TTF in patients with non-immunogenic NSQ NSCLC (3.0 vs 4.6 months, p=0.025, HR=0.61, 95% CI 0.39-0.97) and in patients with non-immunogenic tumors and OR after first-line chemotherapy (3.1 vs 5.3 months, p=0.029, HR=0.56, 95% CI 0.33-0.95).

Figure 7:
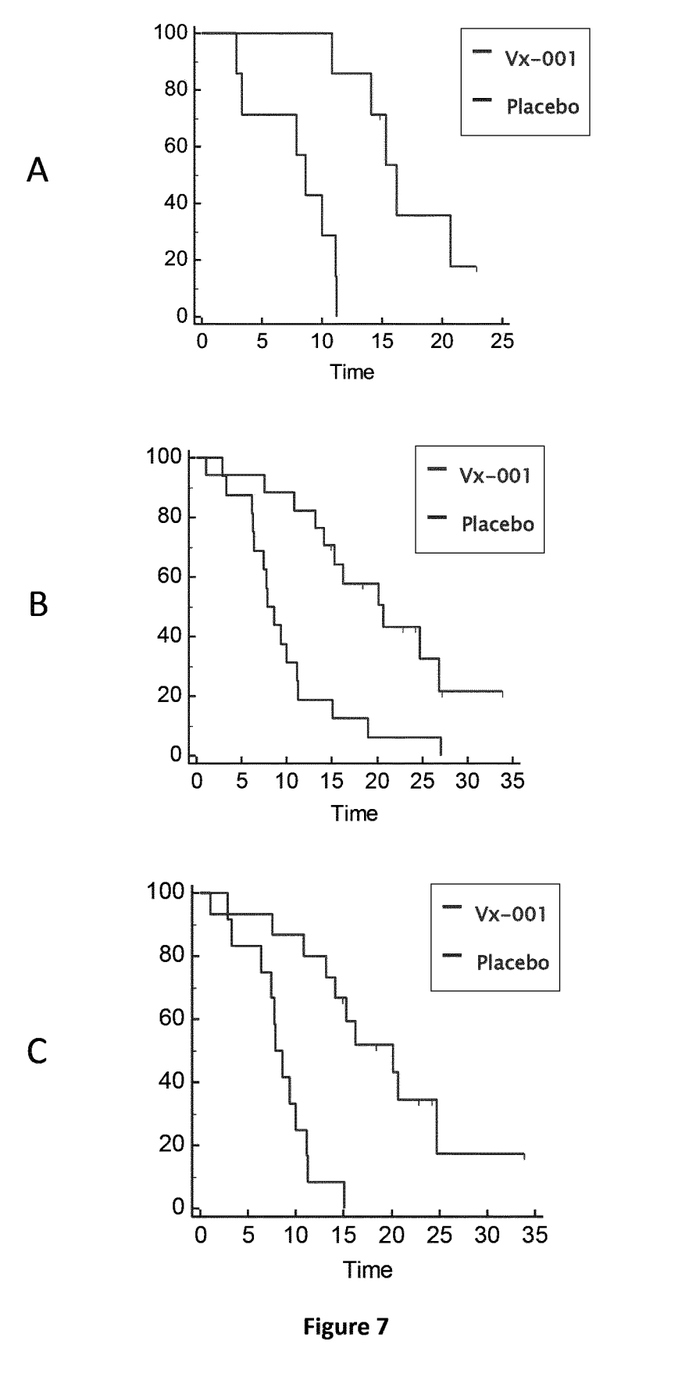
FIG. 7: Clinical outcome of never-smokers and former smokers without natural immunity. A: Never smokers; 8.6 vs 16.2 mo; p=0.0008; HR=0.2 (0.05-0.79). B: Never smokers and former smokers who have been smoking during less than 25 years; 7.9 vs 20.7 mo; p=0.0007; HR=0.29 (0.13-0.67). C: Never smokers and former smokers who have been smoking during less than 20 years; 7.9 vs 20.2 mo; p=0.0001; HR=0.23 (0.08-0.64).

The smoking history of the patients with non-immunogenic tumors is obviously an important parameter, since Vx-001 significantly prolonged survival in never-smoker patients with non-immunogenic tumors (8.6 vs 16.2 months, p=0.0008, HR=0.2, 95% CI 0.02-0.79) (FIG. 7A), in patients with non-immunogenic tumors who either never smoked or have been smokers during less than 25 years (7.9 vs 20.7 months, p=0.0007, HR=0.29, 95% CI 0.13-0.67) (FIG. 7B), and in patients with non-immunogenic tumors who either never smoked or have been smokers during less than 20 years (7.9 vs 20.2 months, p=0.0001, HR=0.23, 95% CI 0.08-0.64) (FIG. 7C). A significant survival prolongation was also observed in patients with non-immunogenic tumors who either never smoked or have been smokers during less than 25 or 30 years. Moreover, there was a significant difference in TTF in patients with non-immunogenic tumors who either never smoked or have been smokers during less than 20 years (3.3 vs 5.6 months, p=0.005, HR=0.39, 95% CI 0.16-0.95), and in patients with non-immunogenic tumors who either never smoked or have been smokers during less than 25 years (3.1 vs 5.6 months, p=0.006, HR=0.43, 95% CI 0.20-0.92).

A trend of significativity was observed in male patients with non-immunogenic tumors (3.1 vs 3.7 months, p=0.09, HR=0.7, 95% CI 0.46-1.06) and in elderly patients with non-immunogenic tumors (3.1 vs 4.4 months, p=0.08, HR=0.65, 95% CI 0.40-1.07). Finally, there was a significant difference in 12 months survival in patients with non-immunogenic NSQ tumors (56.7% vs 30.8%, p=0.036), and in patients with non-immunogenic tumors and OR after 1st line chemotherapy (59% vs 25%, p=0.034), in male patients with non-immunogenic tumors (56.4% vs 32%, p=0.03) and in elderly patients with non-immunogenic tumors (57.1% vs 29.4%, p=0.039) (Tables 7 and 8).

TABLE 7

| | Clinical outcome of sub-groups of patients without natural immunity (OS) | | | | | | | |
|---|---|---|---|---|---|---|---|---|
| | Median survival (months) | | | | | 12 months OS % | | |
| Sub-group | Placebo | Vx-001 | P value | HR | 95% CI | Placebo | Vx-001 | P value |
| Histology | | | | | | | | |
| NSQ (n = 76) | 7.7 | 13.4 | 0.034 | 0.58 | 0.35-0.97 | 30.8 | 56.7 | 0.036 |
| SQ (n = 46) | 9.3 | 13.2 | 0.28 | 1.41 | 0.73-2.73 | 44.4 | 52.6 | 0.76 |
| Response to chemotherapy | | | | | | | | |
| OR (n = 55) | 8.6 | 13.2 | 0.3 | 0.72 | 0.39-1.32 | 38.9 | 57.9 | 0.25 |
| SD (n = 67) | 7.1 | 13.6 | 0.48 | 0.82 | 0.47-1.42 | 33.3 | 54 | 0.32 |
| 1st line chemotherapy | | | | | | | | |
| CARBO (n = 74) | 8.9 | 13.1 | 0.89 | 1.03 | 0.61-1.74 | 42.8 | 53 | 0.48 |
| CDDP (n = 46) | 7.1 | 13.4 | 0.032 | 0.51 | 0.26-0.98 | 25 | 59 | 0.034 |
| Age | | | | | | | | |
| >65 years (n = 63) | 8.1 | 14.1 | 0.11 | 0.63 | 0.36-1.11 | 29.4 | 57.1 | 0.039 |
| <65 years (n = 59) | 9.3 | 12.7 | 0.98 | 1.00 | 0.56-1.79 | 41.9 | 53.6 | 0.43 |
| Sex | | | | | | | | |
| Male (n = 89) | 8.1 | 14.1 | 0.14 | 0.70 | 0.44-1.12 | 32 | 56.4 | 0.030 |
| Female (n = 33) | 11.2 | 12.7 | 0.6 | 1.24 | 0.55-2.77 | 50 | 52.9 | 1 |
| Smoking status | | | | | | | | |
| Never smoker (NS) | 8.6 | 16.2 | 0.0008 | 0.2 | 0.05-0.79 | 0 | 85.7 | 0.004 |
| NS + Former smoker (≤20 years) | 7.9 | 20.2 | 0.0001 | 0.23 | 0.08-0.64 | 8 | 80 | 0.0003 |
| NS + Former smoker (≤25 years) | 7.9 | 20.7 | 0.0007 | 0.29 | 0.13-0.67 | 18.7 | 82.3 | 0.0004 |
| NS + Former smoker (<30 years) | 7.9 | 20.2 | 0.005 | 0.37 | 0.17-0.80 | 22 | 78 | 0.002 |

TABLE 7-continued

Clinical outcome of sub-groups of patients without natural immunity (OS)

| Sub-group | Median survival (months) | | P value | HR | 95% CI | 12 months OS % | | P value |
|---|---|---|---|---|---|---|---|---|
| | Placebo | Vx-001 | | | | Placebo | Vx-001 | |
| Current smoker | 8.3 | 6.4 | 0.50 | 1.3 | 0.56-3.01 | 42.3 | 20 | 0.27 |
| NS or light smoker (≤25 years, former or current smoker) | 9.3 | 20.7 | 0.0001 | 0.27 | 0.12-0.58 | 21.0% | 83.0% | 0.0002 |
| Heavy smoker (>25 years, former or current smoker) | 8.9 | 9.9 | 0.55 | 1.15 | 0.71-1.85 | 42.5% | 42.1% | 0.99 |

TABLE 8

Clinical outcome of sub-groups of patients without natural immunity (TFF)

| Sub-group | Median TTF (months) | | P value | HR | 95% CI |
|---|---|---|---|---|---|
| | Placebo | Vx-001 | | | |
| Histology | | | | | |
| NSQ (n = 78) | 3 | 4.6 | 0.025 | 0.61 | 0.39-0.97 |
| SQ (n = 46) | 3.3 | 3 | 0.56 | 1.18 | 0.65-2.14 |
| Response to chemotherapy | | | | | |
| OR (n = 55) | 3.1 | 5.3 | 0.029 | 0.56 | 0.33-0.95 |
| SD (n = 67) | 3 | 3.6 | 0.85 | 0.95 | 0.59-1.55 |
| 1st line chemotherapy | | | | | |
| CARBO (n = 74) | 3.3 | 3.7 | 0.35 | 0.80 | 0.51-1.27 |
| CDDP (n = 46) | 2.8 | 4.1 | 0.15 | 0.67 | 0.37-1.20 |
| Age | | | | | |
| >65 years (n = 63) | 3.1 | 4.4 | 0.08 | 0.65 | 0.40-1.07 |
| <65 years (n = 59) | 3 | 3.5 | 0.50 | 0.84 | 0.5-1.41 |
| Sex | | | | | |
| Male (n = 89) | 3.1 | 3.7 | 0.09 | 0.70 | 0.46-1.06 |
| Female (n = 33) | 3 | 4.6 | 0.78 | 0.91 | 0.46-1.81 |
| Smoking status | | | | | |
| Never smoker | 3.3 | 5.6 | 0.16 | 0.51 | 0.17-1.55 |
| Former smoker (≤20 years) | 3.3 | 5.6 | 0.005 | 0.39 | 0.16-0.95 |
| Former smoker (≤25 years) | 3.1 | 5.6 | 0.006 | 0.43 | 0.20-0.92 |
| Former smoker (<30 years) | 3.1 | 4.2 | 0.05 | 0.55 | 0.28-1.09 |
| Current | 2.9 | 4.4 | 0.32 | 0.70 | 0.35-140 |

REFERENCES

Al-Shibli K I, Donnem T, Al-Saad S, Persson M, Bremnes R M, Busund L T. *Prognostic effect of epithelial and stromal lymphocyte infiltration in non-small cell lung cancer*. Clin Cancer Res. 2008 Aug. 15; 14(16):5220-7.

Andersen M H and Thor S P. *Survivin—a universal tumor antigen*. Histol Histopathol. 2002 April; 17(2):669-75.

Cesson V, Rivals J P, Escher A, Piotet E, Thielemans K, Posevitz V, Dojcinovic D, Monnier P, Speiser D, Bron L and Romero P. *MAGE-A3 and MAGE-A4 specific CD4(+) T cells in head and neck cancer patients: detection of naturally acquired responses and identification of new epitopes*. Cancer Immunol Immunother. 2011 January; 60(1):23-35.

Coulie P G, Van den Eynde B J, van der Bruggen P and Boon T. *Tumour antigens recognized by T lymphocytes: at the core of cancer immunotherapy*. Nat Rev Cancer. 2014 February; 14(2):135-46.

Fehrenbacher L, Spira A, Ballinger M, Kowanetz M, Vansteenkiste J, Mazieres J, Park K, Smith D, Artal-Cortes A, Lewanski C, Braiteh F, Waterkamp D, He P, Zou W, Chen D S, Yi J, Sandler A, Rittmeyer A *Atezolizumab versus docetaxel for patients with previously treated non-small-cell lung cancer (POPLAR): a multicentre, open-label, phase 2 randomised controlled trial*. Lancet. 2016 Apr. 30; 387(10030)1837-46.

Fridman W H, Galon J, Dieu-Nosjean M C, Cremer I, Fisson S, Damotte D, Pagès F, Tartour E, Sautès-Fridman C. *Immune infiltration in human cancer: prognostic significance and disease control*. Curr Top Microbiol Immunol. 2011; 344:1-24.

Ma W, Vigneron N, Chapiro J, Stroobant V, Germeau C, Boon T Coulie P G and Van den Eynde B J. *A MAGE-C2 antigenic peptide processed by the immunoproteasome is recognized by cytolytic T cells isolated from a melanoma patient after successful immunotherapy*. Int. J. Cancer 2011 129, 2427-2434.

Menez-Jamet J, Gallou C, Rougeot A and Kosmatopoulos K. *Optimized tumor cryptic peptides: the basis for universal neo-antigen-like tumor vaccines*. Ann Transl Med. 2016 July; 4(14):266.

Pagès F, Kirilovsky A, Mlecnik B, Asslaber M, Tosolini M, Bindea G, Lagorce C, Wind P, Marliot F, Bruneval P, Zatloukal K, Trajanoski Z, Berger A, Fridman W H, Galon J. *In situ cytotoxic and memory T cells predict outcome in patients with early-stage colorectal cancer*. J Clin Oncol. 2009 Dec. 10; 27(35):5944-51.

Rizvi N A, Hellmann M D, Snyder A, Kvistborg P, Makarov V, Havel J J, Lee W, Yuan J, Wong P, Ho T S, Miller M L, Rekhtman N, Moreira A L, Ibrahim F, Bruggeman C, Gasmi B, Zappasodi R, Maeda Y, Sander C, Garon E B, Merghoub T, Wolchok J D, Schumacher T N, Chan T A. *Cancer immunology. Mutational landscape determines sensitivity to PD-1 blockade in non-small cell lung cancer*. Science. 2015 Apr. 3; 348(6230)124-8.

Salazar L G, Coveler A L, Swensen R E, Gooley T A, Goodell V, Schiffman K and Disis M L. *Kinetics of tumor-specific T-cell response development after active immunization in patients with HER-2/neu overexpressing cancers*. Clin Immunol. 2007 December; 125(3):275-80.

Soo R A. *Shedding light on the molecular determinants of response to anti-PD-1 therapy*. Transl Lung Cancer Res. 2015 December; 4(6):816-9.

Speiser D E, Rimoldi D, Batard P, Liénard D, Lejeune F, Cerottini J C and Romero P. *Disease-driven T cell activation predicts immune responses to vaccination against melanoma*. Cancer Immun. 2003 Sep. 9; 3:12.

Wang E, Bedognetti D, Marincola F M. *Prediction of response to anticancer immunotherapy using gene signatures*. J Clin Oncol. 2013 Jul. 1; 31(19):2369-71.

The invention claimed is:

1. A method of treating cancer in an HLA-A*0201-positive patient having a tumor expressing Telomerase Reverse Transcriptase (TERT), comprising:
providing a blood sample comprising Cytotoxic T lymphocytes (CTLs) from the patient collected less than 2 weeks after the end of a platinum-based first line chemotherapy and measuring an anti-tumor CTL response, wherein the CTLs in the blood sample have no response specific for the peptide of SEQ ID NO: 1 and/or the peptide of SEQ ID NO: 3 and/or the peptide of SEQ ID No: 5; and
administering 2 vaccinations with the peptide of SEQ ID No: 2 and then 4 vaccinations with the peptide of SEQ ID NO: 1 to the patient, with a three week interval between said vaccinations,
wherein the administration significantly prolongs survival of the patient as compared to placebo.

2. The method of claim 1, wherein said patient has non-small cell lung cancer (NSCLC).

3. The method of claim 2, wherein said patient has non-squamous (NSQ) NSCLC.

4. The method of claim 1, wherein said patient is a never-smoker or a former smoker who had been smoking less than 30 years.

5. The method of claim 1, wherein said patient is a never-smoker or a light-smoker.

6. The method of claim 1, wherein said patient has received a platinum-based chemotherapy and responded thereto prior to vaccination with the peptide of SEQ ID No: 2.

7. The method of claim 1, wherein said patient is more than 65 years old.

8. The method of claim 1, wherein said patient is a male.

9. The method of claim 1, comprising measuring CTL response specific for the peptide of SEQ ID No: 1.

10. The method of claim 9, wherein CTL response specific for the peptide of SEQ ID No: 1 is measured by enzyme-linked immunospot (ELISpot) IFNg assay.

11. The method of claim 1, comprising measuring CTL response specific for the peptide of SEQ ID NO: 3.

12. The method of claim 1, comprising measuring CTL response specific for the peptide of SEQ ID NO: 5.

* * * * *